United States Patent [19]
Glassman

[11] Patent Number: 5,137,525
[45] Date of Patent: Aug. 11, 1992

[54] TEARABLE ANTI-RASH DIAPER CONSTRUCTION

[76] Inventor: Jacob A. Glassman, 1680 Michigan Ave., Miami Beach, Fla. 33139

[21] Appl. No.: 619,396

[22] Filed: Nov. 29, 1990

Related U.S. Application Data

[63] Continuation-in-part of Ser. No. 531,463, May 31, 1990, abandoned.

[51] Int. Cl.⁵ ............................................. A61B 13/15
[52] U.S. Cl. ............................... 604/385.1; 604/385.2; 604/387; 604/389
[58] Field of Search ............... 128/155, 156, 849, 856, 128/853, 854; 664/358, 360, 364, 367, 369–373, 378–385.2, 386, 387, 393–397

[56] References Cited

U.S. PATENT DOCUMENTS

| | | | |
|---|---|---|---|
| 3,085,572 | 4/1963 | Blackford | 128/156 |
| 3,585,999 | 6/1971 | Wanberg | 64/385 |
| 3,667,466 | 6/1972 | Ralph | 128/287 |
| 3,853,598 | 10/1974 | Raguse | 128/156 |
| 3,952,745 | 4/1976 | Duncan | 604/364 |
| 4,135,023 | 1/1979 | Lloyd et al. | 128/156 |
| 4,341,216 | 7/1982 | Obenour | 604/370 |
| 4,346,700 | 8/1982 | Dunshee et al. | 128/155 |
| 4,423,184 | 12/1983 | Kopolow et al. | 604/372 |
| 4,619,649 | 10/1986 | Roberts | 604/396 |
| 4,622,036 | 11/1986 | Goodrum | 604/379 |
| 4,753,840 | 6/1988 | Van Gompel | 428/171 |
| 4,772,499 | 9/1988 | Greenway | 428/43 |
| 4,834,741 | 5/1989 | Sabee | 604/385.2 |
| 4,964,857 | 10/1990 | Osborn | 604/397 |

*Primary Examiner*—David J. Isabella
*Assistant Examiner*—K. Reichle

[57] ABSTRACT

An anti-rash, tearable baby diaper of improved construction is disclosed which includes a layer of absorbent material covered by a layer of an impervious or breathable material which is prepared to allow tearing of the outer layer along lines or curves. The outer layer is substantially unattached to the inner layer or is rupturably unattachable to the outer layer. Upon tearing of the outer layer of material, relatively large yawning gaps or openings are created to allow exposure of the inner absorbent material. The torn areas allow trapped, hot air to escape and the absorbent material to dry, cool, and maintain a reduced temperature in order to prevent "baby diaper rash."

26 Claims, 2 Drawing Sheets

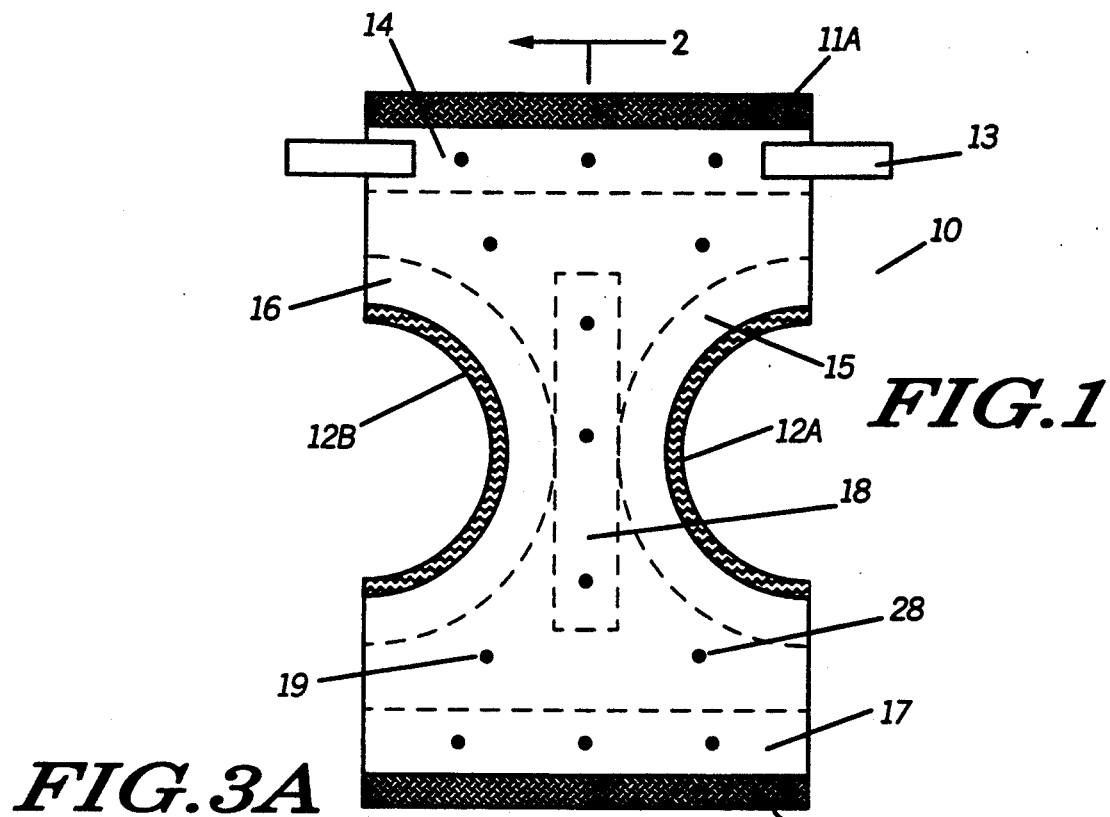
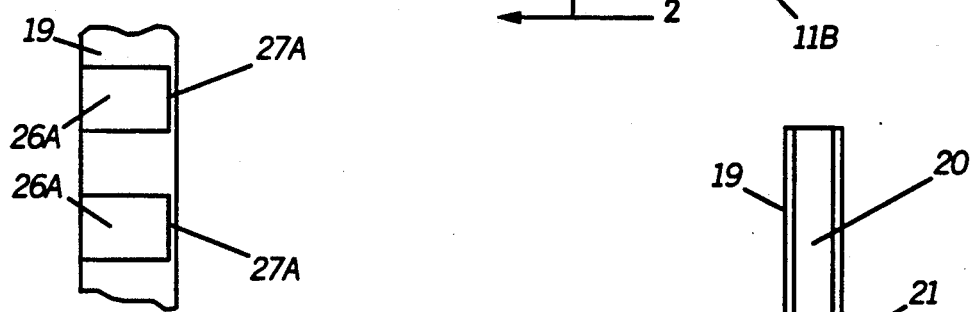
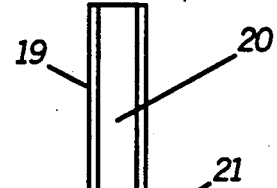
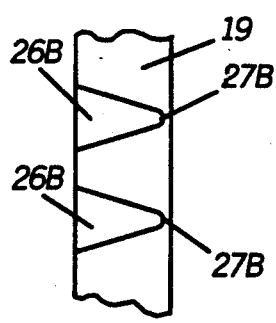
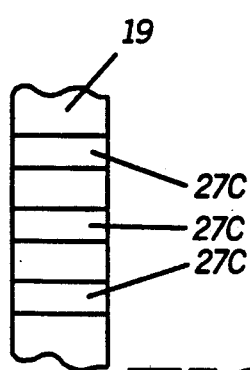

TEARABLE ANTI-RASH DIAPER CONSTRUCTION

CROSS-REFERENCE TO RELATED APPLICATION

This application is a continuation-in-part of prior U.S. application Ser. No. 531,463, filed May 31, 1990, by Jacob A. Glassman, and now abandoned.

BACKGROUND OF THE INVENTION

1. Field of the Invention

This invention pertains in general to the field of disposable diapers and in particular to the field of anti-rash diapers which provide for the creation of openings in the outer layer to release pent-up heat and to allow air drying and thereby prevent diaper rash.

2. Description of the Prior Art

In general, there are two prior art diapers in existence. A disposable diaper made out of various plastic compositions and a non-disposable diaper usually made from a soft material such as cotton. Plastic disposable diapers are by far the most widely used in the various civilized countries. Convenience of use and disposal after use are the keynotes for the wide acceptance of such diapers.

The main object of any diaper is, of course, to absorb any liquid waste, such as urine, while retaining a solid excrement within the confines of the diaper. Quite often, fecal excrement includes a combination of both liquid and a solid. In this instance it is still highly desirable to maintain the solid portion thereof within the confines of the diaper while allowing the liquid portion thereof to be absorbed by the diaper.

Without question, the advances in the prior art diapers substantially prevent the seepage of any liquid or solid from the waist and leg openings of the diaper proper. One contributing factor to this accomplishment is the use of a broad band of an elastic material around each of the waist portions and the thigh portions of the diaper. Use of such elastic material ensures an effective seal or air-tight fitting between the child's body and the diaper.

The above-described prior art diapers are, however, not without certain disadvantages. The confinement of the liquid and solid excrement within the air-tight confines of a diaper necessarily exposes the child's skin to strong irritating substances. In the case of urine, the presence of ammonia therein is irritative and, therefore, detrimental to the child's delicate skin. Similarly, the bacteria within the liquid and/or solid waste matter is also detrimental to the child's skin because they further the irritation process. Further, the complete retention of the liquid and the solid substances within the sealed, air-tight confines of the diaper in combination with the pent-up body heat generated by a child, tend to elevate the temperature within the confines of the diaper which predisposes the diaper wastes to become a breeding ground for various bacteria. All these potential factors contribute to what is commonly known as "baby's diaper rash" which, in turn, can cause a mild to very severe dermatitis. The prior art disposable diapers, unfortunately, contribute to, rather than alleviate the occurrence of "baby's diaper rash."

The use of the prior art disposable diapers during periods of time which involve long time periods such as nighttime when the child is sleeping, traveling by automobile or airplane where it is inconvenient to often change a child's diaper, or while a mother is shopping where it is also inconvenient to often change a child's diaper, are all situations which contribute to the development and spread of a diaper rash. The causative factors are essentially the confined bacterial contaminants, the excessive body heat, and the child's mixed chemically-irritative waste products.

Accordingly, a primary objective of the present invention is to provide a disposable diaper which allows for breathability or the passage of air therethrough in either direction while the diaper is being worn by a child.

Another object of the present invention is to provide a disposable children's diaper which eliminates the problem of a heat buildup within the diaper when being worn by a child over protracted periods of time.

Another object of the present invention is to provide a disposable children's diaper which retains fluid and solid waste therewithin while allowing for breathability and the prevention of excessive heat buildup while being worn by a child over a reasonably long period of time.

Another object of the present invention is to provide a disposable children's diaper which allows for the tearing open of, the outer layer of the diaper to create openings for allowing air passage while minimizing the leakage of any liquid from therewithin, and which allow for an immediate release of heat without incurring leakage of the baby's waste products.

Another object of the present invention is to provide a disposable children's diaper which allows substantial exposure of the absorbing inner layer of fluff material, preferably in selected locations, so as to allow air drying of the fluff material.

The above-stated objects as well as other objects which, although not specifically stated, but are intended to be included within the scope of the present invention, are accomplished by the present invention and will become apparent from the hereinafter set forth Detailed Description of the Invention, Drawings, and the claims appended herewith.

SUMMARY OF THE INVENTION

The present invention accomplishes the above-stated objectives as well as others, which may be determined from a fair reading and interpretation of the entire specification herein, and comprises a breathable and disposable baby's diaper The inside portion of the inventive baby's diaper is constructed in a manner whereby a layer of fluff absorbent material includes an outer layer of soft, pliable material which generally retains the fluff material in a fixed position, and allows a liquid waste material to be absorbed by the fluff material Preferably the outer layer is not adhesively attached to the fluff material except, perhaps, for spaced small dots of glue which when ruptured, allow substantial separation between the outer layer and the inner layer. The broad bands around the waist portion of the diaper and the thigh portions of the diaper are elasticized as in the prior art. The outside layer of the inventive child's diaper is preferably breathable, but may be initially non-breathable, and is provided with lineal depressions or small openings in various directions throughout the width and length of the outer layer or at particular locations so as to create breathability and to readily permit tearing of the outer layer of the diaper in one or more of the various directions. By aligning the tearable locations with the different rash-susceptible locations on the baby, the tearing of the outside of the diaper exposes and cools the inner fluff material by the outside air and thereby alleviates the problem of diaper rash.

The breathable characteristics of the outer layer of the diaper allows for the passage of heat and thus further alleviates or further lessens the growth of rash causing bacterium.

Alone or in combination, the breathability of the outer layer of the diaper and the easy tearability of the outer layer along preferred lines or curves thereof serve to substantially eliminate the body heat buildup while prophylactically preventing the advent of "diaper rash" and negate the requirement to disturb and frequently change the child's diaper in order to avoid the The outer layer of breathable material may allow for the release of heat only or allow the release of heat and moisture (vapor).

BRIEF DESCRIPTION OF THE DRAWINGS

Various other objects, advantages, and features of the invention will become apparent to those skilled in the art from the following discussion taken in conjunction with the following drawings, in which:

FIG. 1 comprises a plan view of the inventive disposable diaper when laid out in a two-dimensional flat plane;

FIG. 2 is a cross-sectional view of the diaper of FIG. 1 taken along the line 2—2 thereof;

FIGS. 3A, 3B, and 3C are enlarged cross-sectional views of the encircled portion of the outer layer of material of FIG. 2 showing different types of indentions or through perforations;

DESCRIPTION OF THE PREFERRED EMBODIMENTS

Figure 4:
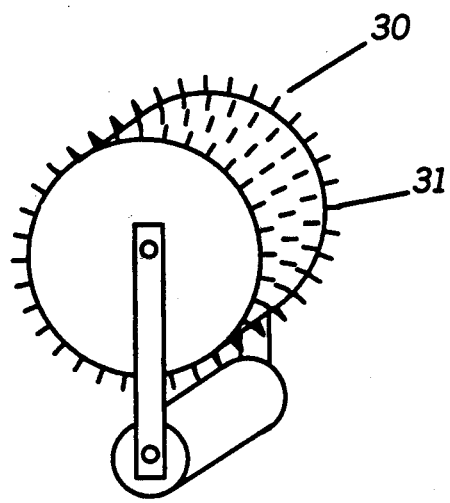
FIG. 4 is a schematic rendition of a surface of a typical tool which may be utilized to incompletely or completely perforate the material from which the outer layer of the inventive diaper is made.

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Reference is now made to the drawings in general, wherein like characteristics and features of the present invention shown in the various figures are designated by the same reference numerals.

Reference is now made specifically to FIG. 1 of the drawings wherein there is shown a plan view of the outside surface of the inventive diaper 10. In overall shape the diaper has an approximate hourglass configuration with the narrow sides (top and bottom) comprising the waist portion 11A and 11B of the diaper and with a pair of oppositely-disposed, semi-circularly formed cutouts 12A and 12B along the long side thereof for fitting around the thigh of the child. Waist portions 11A and 11B and thigh cutout portions 12A and 12B elasticized so as to provide a snug, air-tight fit against body of the child and to prevent seepage of either liquid or solid waste therefrom. A pair of adhesive tabs 13 may be attached at one end to the outside surface 19 of the diaper 10 so as to allow the waist portions 11A and 11B to be snugly secured to each other and around the waist of the child. The areas 14, 15, 16, 17, and 18, defined by dashed lines in FIG. 1, provide locations whereby the outside material 19 of the diaper 10 may be torn apart generally in the longitudinal direction of the areas 14 through, 18 to create openings as hereinafter described in order to simultaneously expose the fluff portion 20 of the diaper to the air and allow the same to be dried and cooled thereby and to eliminate trapped heat from within the diaper.

Figure 6:
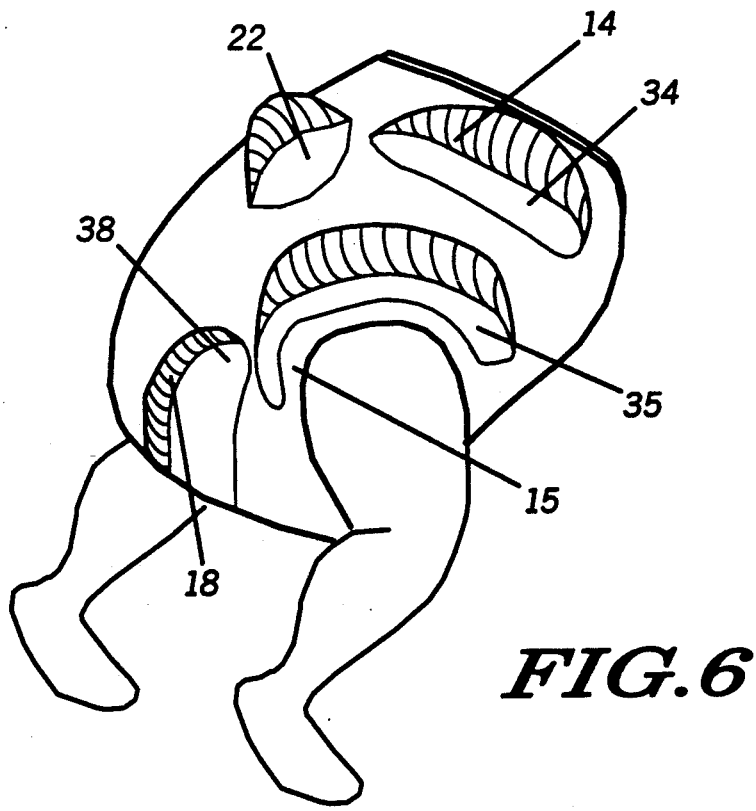

Area 14 extends laterally across the diaper slightly below the upper waist portion 11A the diaper and in the direction of the waist portion 11A and 11B. Area 15 comprises an area surrounding one leg cutout 12A. Area 16 is a mirror image of area 15, but surrounds the other leg cutout 12B. Area 17 extends laterally across the diaper in the direction of lower waist portion 11B. Area 18 is a straight area extending through the crotch of the diaper in a direction parallel to the long axis of the diaper. Areas 14 through 18 contain either a plurality of small incomplete perforations or small holes through the thickness of layer 19 which are generally oriented in lines in the longitudinal direction of areas 14 through 18. Accordingly, diaper 10 may gently be torn apart at any one or all of the area portions 14 through 18 in order to vent the heat buildup and to expose the wet fluff thereunder and allow the same to dry without the need to change the diaper. Torn areas 14 (or 17), 15 (or 16), and 18 are shown in FIG. 6, creating transverse linear waist openings 34, and vertical midline openings 38, and circular openings 35, about thighs respectively of the person wearing the diaper.

In the alternative, the entire surface of outer layer may be made tearable across the entire length and width thereof.

In this manner, outer layer 19 may be torn open at any location or locations across the length and width of outer layer 19 to expose the fluff portion or layer 20 of the diaper to the air and allow the same to be dried by the air and to release any pent-up heat contained within the outer layer 19 of the diaper 10.

FIG. 2 is a cross section of the diaper 10 taken through the line 2—2 of FIG. 1. Layer, 19 comprises the outer layer of diaper 10 which may be made from a breathable material or from an impervious material. Layer 19 may, therefore, comprise a thin sheet of impervious plastic made breathable and tearable at particular locations or across the entire length and width thereof. Or, layer 19 may comprise a breathable material, made tearable at particular locations or across the entire length and width thereof.

Outer layer 19 may be made either breathable or tearable or both breathable and tearable by providing the incomplete perforations shown in FIGS. 3A and 3B, or by providing the through perforation shown in FIG. 3C.

In FIGS. 3A and 3B, a plurality of incomplete perforations 26A or 26B are provided across the thickness of outer layer 19. A thin microporous membrane 27A or 27B is left (across the thickness of outer layer 19) at each of the locations of incomplete perforations 26A or 26B. For example, assuming that the thickness of the outer layer 19 of diaper 10 is approximately 0.007 inches thick, a perforation 26A or 26B of the order of 0.010 to 0.020 of an inch in diameter may extend through the thickness of layer 19 for a distance of approximately 0.0065 inches. This leaves a membrane 27A or 27B of approximately 0.0005 inches thick at the base of the perforation. Each membrane 27A and 27B, due to its thinness, desirably has a porosity in the range of 0.1 to 0.5 microns to allow air but not vapor to pass therethrough. In this regard, the inventive diaper 10 will allow for the release of heat but not moisture from within the diaper 10 to the outside area. Or, membranes 27A and 27B, may have a slightly larger porosity (greater than 0.5 microns) to allow both air and moisture (but not a liquid) ,to pass therethrough. The distance or linear space between perforations 26 may be of the order of 0.005 to 0.020 inches. With the latter porosity, the inventive diaper 10 will allow both heat and a small amount of moisture to escape from the diaper to the outside air.

In FIG. 3C, a plurality of small diameter through holes 26C are shown through the thickness of outer layer 19. Depending upon the size of holes 26C, either air only or both air and moisture (but not a liquid) is allowed to escape from diaper 10, thereby releasing pent-up heat and a small amount of moisture.

By utilizing the incomplete perforations 26A or 26B, or the through perforations 26C across the thickness of an impervious material, the same is made both breathable and tearable. By utilizing the incomplete perforations 26A or 26B, or the through perforations 26C across the thickness of a breathable material, the same is made tearable. Again, the location of the plurality of perforations 26A, 26B or 26C may be provided at particular areas of diaper 10 such as areas 14 through 18, or across the entire length and width of diaper 10.

As stated above, layer 19 may comprise a breathable, fabric which may permit the passage therethrough of air only. One such commercially available material is EVOLUTION ® manufactured by Kimberly Clark ® comprising a meltblown inner layer sandwiched between outside layers of a spun-bond material. Tests by Kimberly Clark ® have shown that the material or fabric EVOLUTION ® provides a superior combination of varied properties with the microfiber center providing an effective bacterial barrier while the outer spun-bond material layers provide for breathability needed to allow the passage of air therethrough.

A breathable layer 19 may, alternatively, comprise a breathable UV polymerized membrane which is made by a recently developed process. This process involves relatively small molecules containing highly-reactive acrylate functional groups, such as diafunctional oligomers and monomers. The important characteristics of these chemical constituents is the fact that when exposed to powerful ultraviolet radiation, polymerization occurs extremely rapidly——within tenths of a second——and forms a microporous structure. Speeds as fast as 1000 feet per minute have been achieved in some industries making fabrics comprising hydrophobic UV polymerized membrane. The relatively instantaneously polymerization of the oligomers and the monomers form a microporous structure which, depending upon the size of the pores, allows the passage of air only or air and vapor, but neither the passage of a liquid nor the passage of a solid.

Again referring to FIG. 2, a fluff material 20, as per the prior art, which readily absorbs moisture, may be sandwiched between an inside 21 layer and outside 19 layer. Other than at waist 11A and 11B and thigh 12A and 12B locations, outside. Layer 19 is preferably not attached to fluff material 20 or may be spot attached thereto by small, spaced spots of glue 28 to minimally but adequately retain fluff material in position. However, if small spots of glue 28 are used, the bond should be such that when, for example, any or all of the outer layer 19 of areas 14 through 18 are torn open, the outer layer 19 is readily separated from the fluff material 20, leaving yawning openings which expose a substantial portion of the fluff material 20 to the air and not covered over by layer 19. In other words, such that a person using his or hand may easily break the bonds created by the small spots of glue 28 and leave the wet fluff layer 20 separated from the outer layer 19 in order to allow a substantial portion of the wet fluff material 20 in the torn-open areas to be exposed to drying air. Layer 21 may comprise, as per the prior art, a porous, soft, tissue-like plastic which is adhesively attached to fluff material 20.

An impervious layer of material 19 made breathable or breathable and tearable by having the not quite-through perforations 26A or 26B located therewithin may be manufactured by a tool such as that schematically shown in FIG. 4. In FIG. 4 the perforation tool 30 may include a rolling surface having a plurality of small protrusions 31, with each protrusion 31 having a shape similar to the inside of the perforations 26A and 26B shown in FIGS. 3A and 3B. Accordingly, tool 30 may consist of a roller which rolls across a flat sheet of impervious plastic (thereby making the same breathable or both tearable and breathable) placing the perforations 26A and 26B therein prior to being fabricated into a shape consistent with the plan view of the diaper shown in FIG. 1 of the drawings.

Figure 5:
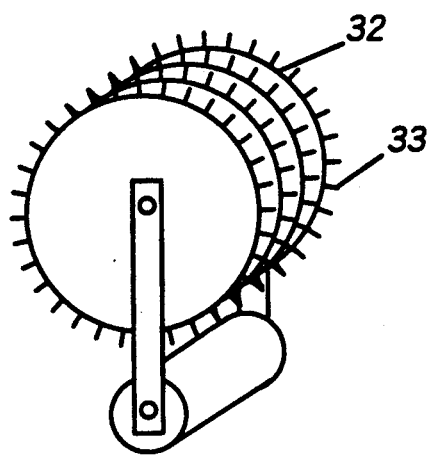
FIG. 5 is a schematic view of another version of a typical tool which may be used to incompletely or completely perforate the outer layer of material of the inventive diaper; and, FIG. 6 is an isometric view of a baby wearing a diaper according to the present invention and where a number of tearable areas are shown in a torn open position.

FIG. 5 shows another perforation tool 32 which may comprise an array of side-by-side disks having a plurality of pointed of flattened protrusions 33 emanating from the circular peripheral surface thereof. Tool 32 may also be used for providing tearability and porosity to an impermeable layer 19 of material thereby providing the outer layer of material 19 with many small not-through holes.

The incomplete perforations created by either of tools 30 or 32 thereby render an impervious material, breathable or breathable and tearable, and a breathable material tearable.

Tools 30 and 32 may also be used to create the through perforations 27C shown in FIG. 3C. In this instance, the protrusions 31 and 33 would comprise a thin needle having a sharpened point to allow penetration completely through an impervious or a breathable layer of outer material 19.

In use, as shown in FIG. 6, when the inventive diaper 10 is attached or fitted to a child, the liquid waste from the child is primarily absorbed by the fluff layer 20 of the diaper 10. A breathable outer layer 19 allows air to pass through layer 19 so as to release pent-up heat from within diaper 10 to escape to the atmosphere and, depending upon the porosity thereof, may allow the fluff material 20 to somewhat dry by allowing vapor to pass through breathable layer 19. An impervious layer of outer material 19 will not normally allow heat or air to pass therethrough; but, when provided with porosity or through perforations, some release of heat and some air drying of the fluff material 20 will occur. In the event that the ability of fluff material 20 to dry is desired to be substantially increased without necessarily changing the diaper 10 on the child, a person (mother or nurse) may simply pinch the layer 19 at opposite sides of any one of the incompletely perforated or through perforated areas 14 through 18 or at any other location 22, and by exerting a slight pulling apart force, tear the outer layer 19 in the transverse or longitudinal direction of any of the areas 14 through 18. Once any of the perforated areas 14 through 18 or any other areas 22 of the diaper 10 are separated or torn apart, and since outer layer 19 is either not attached to fluff material 20 or is minimally attached by spaced small dots of glue which may readily be separated, the contained fluff material 20 at each of these locations is substantially exposed to the air and thereby allows the fluff material 20 to further cool and dry. These features of the inventive diaper 10, thus, substantially diminish the predisposability of a diaper to cause "diaper rash."

It is to be noted that the above-described inventive diaper 10 may be used with either a child or an adult.

While the invention has been described, disclosed, illustrated and shown in certain terms or certain embodiments or modifications which it has assumed in practice, the scope of the invention is not intended to be nor should it be deemed to be limited thereby and such other modifications or embodiments as may be suggested by the teachings herein are particularly reserved especially as they fall within the scope of the breadth and scope of the claims here appended.

I claim as my invention:

1. An anti-rash diaper for use with an adult or a young child, comprising:
   an outer layer of flexible material,
   a co-extensive inner layer of flexible absorbent material overlying said outer layer,
   the combination defining oppositely disposed end portions, means for attaching said end portions to each other, means for making said outer layer breathable, and
   tearable along a line or a curve for creating one or more openings in said outer layer at any location thereon too expose the absorbent material to air and to allow the release of pent-up heat while the adult or child wears the diaper yet not disturbing means for attaching the diaper so the adult or child continues to wear the diaper while prophylactically preventing the advent of diaper rash.

2. The anti-rash diaper of claim 1, wherein said outer layer of flexible material is impervious.

3. The anti-rash diaper of claim 2, wherein said means for making the outer layer breathable and tearable comprises a plurality of indentations in the thickness of said outer layer which leave a membrane at each of the locations of said indentations having porosity which allows the passage of air therethrough.

4. The anti-rash diaper of claim 2, wherein said means for making the outer layer breathable and tearable, comprises a plurality of perforations through the thickness of said outer layer.

5. The diaper of claim 2, wherein said outer layer is not attached to said inner layer except at said end portions.

6. The diaper of claim 2, wherein said outer layer is spot attached to said inner layer with spaces between adjacent spots, said spot attachments being rupturably nonattachable.

7. An anti-rash diaper for use with an adult or a young child, comprising:
   an outer layer of breathable material,
   a co-extensive inner layer of absorbent material overlying said outer layer,
   said combination defining oppositely disposed end portions,
   means for attaching the end portions to each other, and
   means for making the outer layer tearable along a line or a curve at any location on said outer layer of material for creating one or more openings in said outer layer to expose the absorbent material to air while the adult or child wears the diaper and yet not disturb means for attaching so the adult or child continues to wear the diaper while prophylactically preventing the advent of diaper rash.

8. The diaper of claim 7, wherein said outer layer is not attached to said inner layer except at the said end portions.

9. The diaper of claim 7, wherein said outer layer is spot attached to said inner layer with spaces between adjacent spots, said spot attachments being rupturably unattachable.

10. An anti-rash diaper for use with an adult or a young child comprising an outer layer of a flexible material, a co-extensive inner layer of an absorbent flexible material overlying said outer layer, said combination defining oppositely disposes end portions, means for attaching the end portions to each other, and means for tearing said outer layer of material along a line in one or more predetermined areas to create openings in said one or more predetermined areas which expose the absorbent material thereat to air and allow the release of pent-up heat while the adult or child wears the diaper and yet not disturb the means for attaching so the adult or child continues to wear the diaper while prophylactically preventing the advent of diaper rash.

11. The diaper of claim 10, wherein said outer layer comprises a breathable material.

12. The diaper of claim 11, wherein said breathable material comprises an impervious layer of plastic containing a plurality of indentions across the thickness of said outer layer which leave a membrane at each indentation having a porosity which allows the passage therethrough of air but not vapor.

13. The diaper of claim 11, wherein said breathable material comprises an impervious layer of plastic having a plurality of indentions across the thickness of said outer layer which leave a membrane at each indentation having a porosity which allows air and vapor to pass therethrough.

14. The diaper of claim 11, wherein said breathable material comprises an ultraviolet-polymerized material.

15. The diaper of claim 11, wherein said breathable material comprises a layer of spunmelt material sandwiched in between layers of a spun-bonded material.

16. The diaper of claim 10, wherein said outer layer comprises an impervious material.

17. The diaper of claim 16, wherein said means for tearing the outer layer along a line in one or more predetermined areas comprises a plurality of substantially incomplete performations through said layer of material in a direction generally along the predetermined tear line.

18. The diaper of claim 17, wherein said one or more predetermined areas comprises the adult's or child's waist area.

19. The diaper of claim 17, wherein said predetermined area comprises a person's thigh area.

20. The diaper of claim 17, wherein said predetermined area comprises a person's crotch area.

21. The diaper of claim 16, wherein said means for tearing along a line in one or more predetermined areas comprises a plurality of perforations through said outer layer of material in a direction generally along the predetermined tear line.

22. The diaper of claim 21, wherein said predetermined area comprises a person's waist area.

23. The diaper of claim 21, wherein said predetermined area comprises a person's thigh area.

24. The diaper of claim 21, wherein said predetermined area comprises a person's crotch area.

25. The diaper of claim 10, wherein said outer layer is not attached to said inner layer except at the said end portions.

26. The diaper of claim 10, wherein said outer layer is spot attached to said inner layer with spaces between adjacent spots, said spot attachments being rupturably unattachable.

* * * * *